United States Patent [19]

Koeneman et al.

[11] Patent Number: 4,747,400

[45] Date of Patent: May 31, 1988

[54] EXTERNAL FIXATION DEVICE

[75] Inventors: James B. Koeneman, Mesa; Thomas M. Hansen, Phoenix; Mark Phillips, Mesa; Allan M. Weinstein, Paradise Valley, all of Ariz.

[73] Assignee: Harrington Arthritis Research Center, Phoenix, Ariz.

[21] Appl. No.: 791,222

[22] Filed: Oct. 25, 1985

Related U.S. Application Data

[63] Continuation-in-part of Ser. No. 604,047, Apr. 26, 1984, Pat. No. 4,584,995.

[51] Int. Cl.$^4$ .............................................. A61F 5/04
[52] U.S. Cl. .................................. 128/92 Z; 128/84 B
[58] Field of Search ............ 128/92 VD, 92 Z, 92 V, 128/92 YS, 92 YP, 92 YL, 92 YE, 92 YF, 92 R, 84 B; 269/236, 268; 384/17, 21, 23

[56] References Cited

U.S. PATENT DOCUMENTS

| 214,907 | 4/1879 | Grimmitt ............................ 269/268 |
| 2,080,802 | 5/1937 | Anderson . |
| 2,371,519 | 3/1945 | Haynes . |
| 2,398,915 | 4/1946 | Bell . |
| 2,434,431 | 1/1948 | Pincock . |
| 2,697,433 | 12/1954 | Zehnder ......................... 128/92 VD |
| 3,160,448 | 12/1964 | Abernathy et al. ..................... 384/23 |
| 3,547,113 | 12/1970 | Swanson . |
| 3,847,489 | 11/1974 | Van Riper .................... 248/297.2 X |
| 3,866,607 | 2/1975 | Forsythe et al. . |
| 3,877,424 | 4/1975 | Murray . |
| 3,977,397 | 8/1976 | Kalnberz et al. . |
| 4,078,302 | 3/1978 | Fok et al. ........................ 269/236 X |
| 4,244,360 | 1/1981 | Dohogne . |
| 4,308,863 | 1/1982 | Fischer . |
| 4,361,144 | 11/1982 | Slatis et al. . |
| 4,365,624 | 12/1982 | Jaquet . |

FOREIGN PATENT DOCUMENTS

| 2532539 | 6/1976 | Fed. Rep. of Germany . |
| 2718515 | 11/1977 | Fed. Rep. of Germany .... 128/92 Z |
| 2040168 | 8/1980 | United Kingdom .............. 128/92 Z |
| 2086231 | 5/1982 | United Kingdom . |
| 0611612 | 5/1978 | U.S.S.R. ............................ 128/92 Z |
| 0667205 | 6/1979 | U.S.S.R. ............................ 128/92 Z |
| 770487 | 10/1980 | U.S.S.R. . |
| 0829105 | 5/1981 | U.S.S.R. ............................ 128/92 Z |
| 1009445 | 4/1983 | U.S.S.R. ........................ 128/92 VD |
| 1049056 | 10/1983 | U.S.S.R. ........................ 128/92 YL |
| 1149960 | 4/1985 | U.S.S.R. ............................ 128/92 Z |

OTHER PUBLICATIONS

Howmedica, Inc. brochure, "The External Fixation System", pp. 1-32.
E. Y. Chao et al, *J. Biomechanics*, "Rigidity and Stress Analyses of External Fracture Fixation Devices—A Theoretical Approach", vol. 15, No. 12, pp. 971-982.
E. Y. S. Chao et al, *Finite Elements in Biomechanics*, "Biomechanical Analysis of External Fixation Devices for the Treatment of Open Bone Fractures", pp. 195-220.
Mears, Dana C., "External Skeletal Fixation", pp. 1-41.
Ace Medical brochure, "The Ace-Fischer Fixator", pp. 1-12.

*Primary Examiner*—Richard J. Apley
*Assistant Examiner*—David Bender
*Attorney, Agent, or Firm*—Wood, Herron & Evans

[57] ABSTRACT

A unilateral external fixation device for closed reduction of simple or comminuted long bone fractures includes a frame formed of composite materials which mounts a proximal carriage at one end and a distal carriage at the other end. The proximal carriage is adapted to mount half pins inserted in the proximal segment, and is supported on the frame by support arms which are movable with respect to the frame for adjusting the position of the proximal segment. The distal carriage includes a clamping member adapted to mount half pins inserted in the distal segment, which is pivotal about the fracture to permit precise adjustment of the distal segment for alignment with the proximal segment. A fragment support, mounted to one of the side rails of the support arm for the proximal carriage, is adapted to clamp a half pin inserted within a central fragment positioned between the proximal and distal segments of a comminuted fracture.

27 Claims, 5 Drawing Sheets

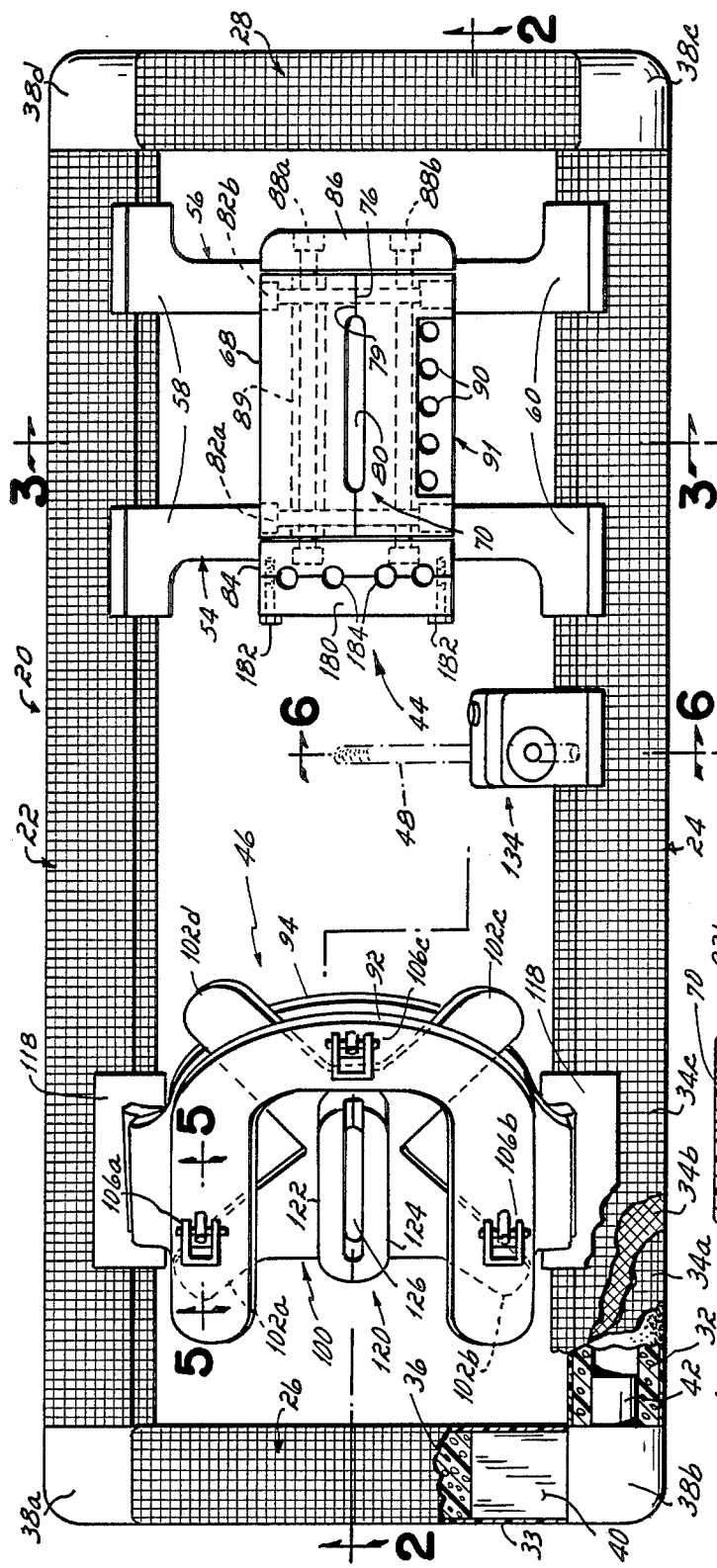
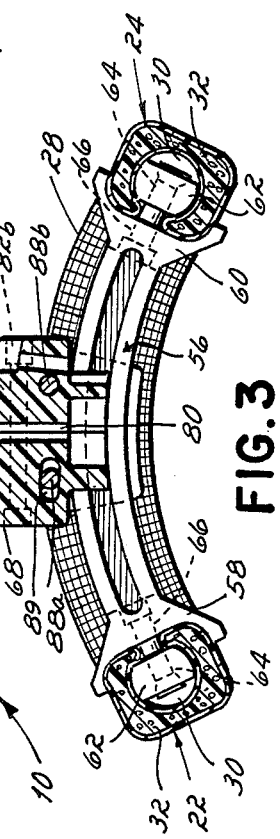

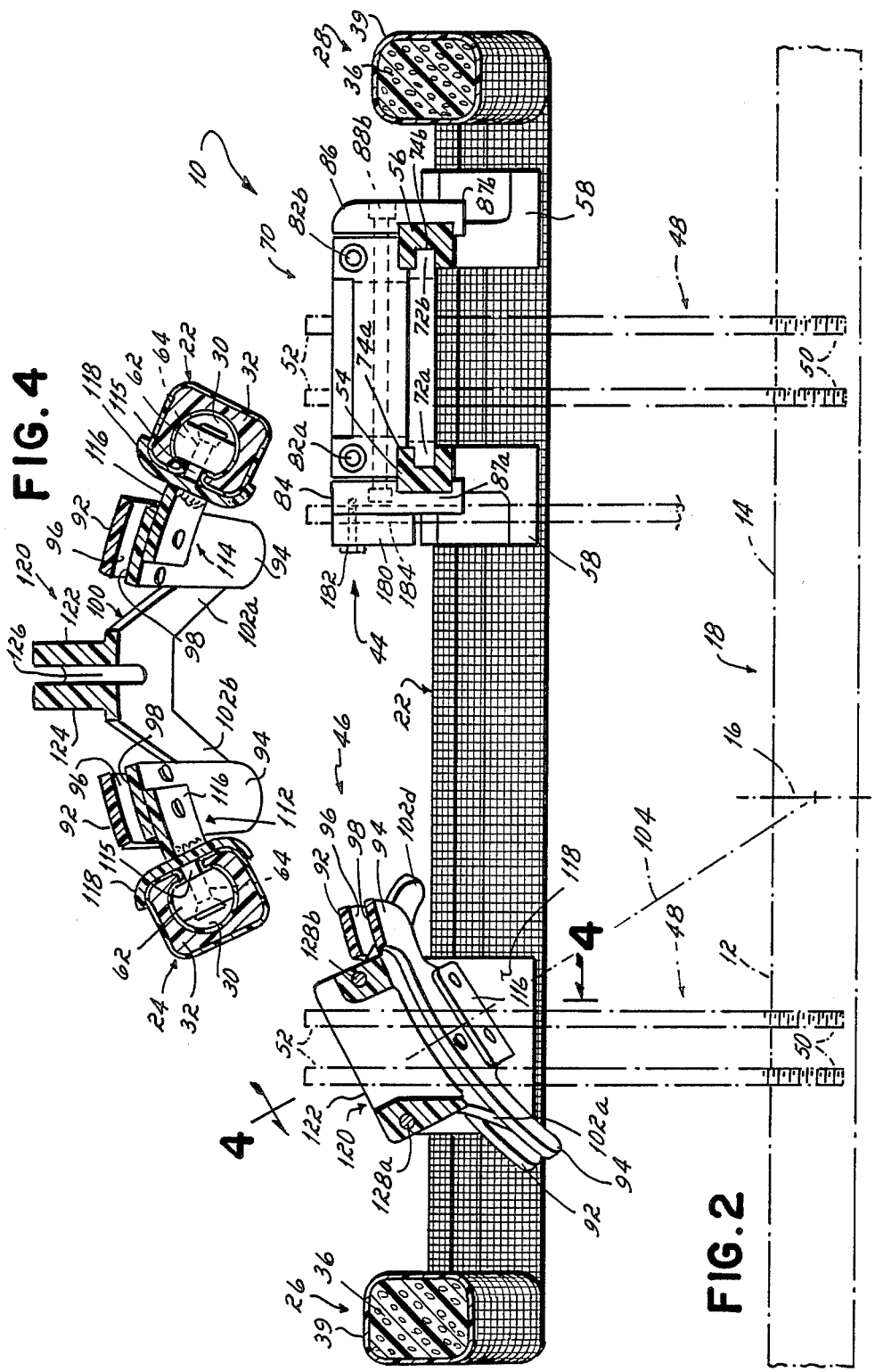

EXTERNAL FIXATION DEVICE

RELATED APPLICATIONS

This application is a continuation-in-part of application Ser. No. 604,047, filed Apr. 26, 1984, and entitled "External Fixation Device" now U.S. Pat. No. 4,584,995 which issued Apr. 29, 1986.

BACKGROUND OF THE INVENTION

This invention relates generally to devices for the treatment of bone fractures in which soft tissue damage is present, and, more particularly, to a pre-assembled, unilateral external fixation device for closed reduction of a bone fracture which is operable to apply controlled distraction and compression at the fracture site of the bone.

A variety of activities such as high speed travel and the widespread use of heavy machinery in industry have in recent years increased the frequency of severely compounded and infected long bone fractures, such as the femur, tibia, radius and ulna, with accompanying damage to the surrounding soft tissue. In order to properly manage the wound and prevent infection of the soft tissue, it is necessary to avoid covering the affected area except with appropriate dressings or skin grafts. Casts may not be used for the treatment of long bone fractures where soft tissue damage is present.

One early method of treatment of these cases, which is still used today, involves placing the patient in traction to completely immobilize the affected limb. As is well known, there are many problems attendant to long term confinement of a patient to a bed including necrotic pressure sores and muscle atrophy.

Another approach in the prior art for the treatment of such fractures involved the use of internal fixation devices such as bone plates which were secured directly to the bone. The problem with this method is that the fracture segments must be exposed to insert and affix the device, which increases the chance of infection of both the bone and surrounding soft tissue.

In order to limit the use of traction in the treatment of fractured bones with attendant soft tissue damage, and to avoid the use of bone plates and other internal fixation devices, research begun in the 1800's resulted in the development of external skeletal fixation devices. These devices generally comprise one or more retaining pins secured to the distal bone segment and proximal bone segment on opposite sides of the fracture, which are adjustably connected to a frame located externally of the affected limb.

One external fixation device commonly used today is the so-called Hoffmann system originally developed in the late 1930's. The Hoffman fixation system includes two sets of self-drilling and self-tapping transfixing pins each having a centrally located continuous thread. One set of two or three pins enters the soft tissue at one side of the fracture site, passes completely through the distal or proximal segment of the bone and then extends outwardly through the soft tissue on the opposite side. The same procedure is repeated for the other set of transfixing pins on the opposite side of the fracture. Each transfixing pin is connected at opposite ends to a frame which is adapted to permit translation and pivoting of the pins for properly aligning the distal and proximal segments. The frame is adjustable during the surgical procedure, and controlled distraction or compression may be applied post-operatively to maintain the segments in engagement and in alignment.

Known external fixation device incorporate different frame configurations for supporting the transfixing pins such as bilateral, triangular, circular and quadrilateral frames. The above-described Hoffmann device employs a quadrilateral frame. In each of these prior art fixation devices, transfixing pins are used to support the fractured bone segments, which, as described above, extend completely through the soft tissue and bone in the affected limb.

Several problems are encountered with the use of transfixing pins, and with the various frame designs for mounting the pins inserted in the distal or proximal bone segments. Assume a patient has a femoral fracture with substantial soft tissue damage at one or more locations along the thigh. The transfixing pins are first inserted into the soft tissue on the distal and proximal side of the fracture. The surgeon can manipulate each transfixing pin around nerves and arteries in the soft tissue until it contacts the femur and begins to enter the cortical bone. At that point, the path of the pin is fixed and no further manipulation is possible. There is a substantial risk of nerve and arterial damage as the pin passes through the femur and then through the soft tissue in a fixed path on the opposite side of the leg. Each of the quadrilateral, circular, triangular and bilateral external fixation devices utilizes transfixing pins.

A second major problem with prior art external fixation devices, and particularly the Hoffmann device, is that the frame elements for supporting the transfixing pins are not preassembled but must be assembled during the surgery. An assortment of clamping elements and adjustment mechanisms forming the Hoffmann frame are provided in separate pieces and must be fitted together and then clamped to the transfixing pins during the surgical procedure. It has been found that unless a surgeon has great familiarity with the Hoffmann device, or other unassembled frame devices, there may be a reluctance to employ an external fixation device at all.

One purpose of external fixation devices is to enable patients to move about and reduce the incidence of necrosis and other problems caused by confinement to bed. Many of the frame designs for securing transfixing pins, including the Hoffmann quadrilateral system and circular frames such as shown in U.S. Pat. Nos. 4,365,624 and 4,308,863, are extremely bulky and make it difficult for the patient to walk or otherwise move about. It addition, bulky metal frames often cover the fracture site and obstruct x-rays. While the transfixing pins must be firmly secured to apply the necessary force to the bone segments, it is desirable to make the frame as light as possible without obstructing the fracture site.

Another disadvantage of external fixation devices is the difficulty in adjusting the position and force exerted by the retaining pins, both during and after surgery. During a surgical procedure and post-operatively, external fixation devices must be capable of adjusting the transfixing pins to vary the position of the bone segments and to control distraction and compression at the fracture site. It is often desirable to make relatively minor corrections of the position or force exerted by a set of retaining pins on one side of the fracture. However, in the Hoffmann quadrilateral fixation device, for example, movement of the frame elements to adjust the position of one set of transfixing pins in any direction requires adjustment of other frame elements associated with the other set of transfixing pins. This feature of the Hoffman device unduly complicates post-operative adjustment procedures which further reduces the willingness of physicians to employ such device.

Some of the problems with external fixation devices employing transfixing pins described above have been eliminated by unilateral fixation devices which secure half pins mounted in the bone fragments. Half pins extend into only one side of the extremity and are held in place by a unilateral frame which is also mounted on only one side of the affected limb. Unilateral fixation devices are generally lighter in weight and present less of an obstruction to the affected area than other external fixation devices, but other problems are created. Many unilateral fixation devices do not provide the desired stability to prevent movement of the bone segments relative to one another, particularly axial rotation and transverse subluxation of the segments.

In addition, fine or small adjustment of the position of the bone segments at the fracture is often difficult with unilateral fixation devices. Slight adjustment of the position of the half pins at the frame in prior art unilateral devices results in substantial movement of the bone segment connected to such half pins at the fracture site. Gross adjustment of the segment positions is made by the surgeon by hand, and it is thus desirable to make only fine adjustments in the position of the segments once the fixation device is in place.

SUMMARY OF THE INVENTION

It is therefore among the objects of this invention to provide a unilateral external fixation device for positioning and immobilizing the distal segment and proximal segment of a fractured bone for closed reduction of the fracture, which is light weight, which is preassembled, which employs half pins for securing the proximal and distal segments, which permits easy access to the affected area for treatment of the soft tissue and to permit the taking of x-rays, and which permits fine adjustment of the position of at least the distal segment at the fracture site.

These objectives are accomplished in an external fixation device which comprises a frame having a proximal carriage mounted at one end and a distal carriage mounted at the other end. A set of half pins, each having a threaded end inserted into the cortical bone of the proximal segment and a smooth end extending outwardly from the limb, are clamped in place by the proximal carriage. The proximal carriage is movable with respect to the frame to adjust the position of the proximal segment at the fracture site. Similarly, a second set of half pins are secured to the distal segment whose ends are clamped and immobilized by the distal carriage. As described in more detail below, a clamping element of the distal carriage is pivotal about the fracture so as to permit fine adjustment of the position of the distal segment at the fracture for anatomically correct alignment with the proximal segment.

More specifically, in a presently preferred embodiment of this invention the frame is generally rectangular shaped having two side rails connected at each end to a pair of opposed, arcuate end rails. Each of the side rails is formed with a generally C-shaped cross section having a generally circular, open interior, while the end rails have a solid interior. In an alternative embodiment, the side rails are formed in a circular cross section with a solid, closed center. Preferably, the side rails and end rails in both embodiments are formed with a core of foam material, such as polyimide foam, and a plurality of outer layers of composite material wrapped about the foam core. The composite outer layers are wrapped about the core at angles of 0° and 45° relative to its longitudinal axis, and are preferably formed of graphite or glass fibers impregnated with a thermosetting matrix material such as epoxy, or a thermoplastic matrix material such as polysulfone. Alternatively, the outer layer of composite material could be formed of one or two layers of woven or unidirectional fiber reinforced composite material.

In a further aspect of this invention, alignment of the proximal bone segment is achieved by movement of the proximal carriage with respect to the frame. The proximal carriage comprises a pair of pin clamping sections having abutting walls each formed with a notch which together form a slot oriented substantially parallel to the side rails of the frame for receiving the outwardly extending end of the half pins mounted in the proximal segment. The pin clamping sections are releasably secured together to mount the half pins within the slot by a pair of screws which extend from one pin clamping section into the other.

The proximal carriage is mounted to the frame by a pair of arcuate, support arms whose end sections are each adapted to slidably engage one of the side rails for movement along the longitudinal axis of the frame. The pin clamping sections of the proximal carriage are slidably mounted upon the support arms by a pair of end caps which are disposed at opposite ends of the pin clamping sections and releasably mount to the support arms. Preferably, at least one of the end caps is formed with a number of spaced, transverse bores oriented substantially perpendicularly to the side rails of the frame. Each bore is adapted to receive an end of a half pin and includes means for clamping the half pin thereto. The transverse bores are used in instances where the fracture is near the joint of a bone and the proximal segment is therefore small and not long enough to receive half pins clamped by the notch between the pin clamping sections. The proximal carriage is therefore movable with the support arms along the longitudinal axis of the side rails, and is also movable perpendicularly to the side rails along the support arms for positioning of the proximal bone fragment in the desired location.

In an alternative embodiment, the proximal carriage is provided with a compliance assembly which functions both to permit relatively small axial adjustments of the proximal carriage along the side rails and also to introduce compliance into the fixation device. The compliance assembly includes a brace movable along one of the end rails which receives one end of a rod formed with a head. The other end of the rod is threaded into the proximal carriage.

The compliance assembly also includes a compression spring disposed between the head of the rod and the brace. The purpose of the compression spring is to introduce compliance to the frame at desired stages of healing of the fractured bone, and to permit at least some axial adjustment of the proximal carriage relative to the longitudinal axis of the frame. During the initial stages of treatment, the proximal carriage is clamped in a fixed position to the frame. Forces applied by the patient's weight in walking or moving about, assuming the femur is fractured, are therefore transferred from the proximal femoral segment, to the proximal carriage, along the side rails of the frame and then through the distal carriage to the distal femoral segment. Little or no load is applied to the fracture itself, and the frame thus acts like a bridge over the fracture site.

As is well known, fractures tend to heal better if at least some load is applied urging the adjacent segments against one another at the fracture. In order to provide such loading at the fracture, the proximal carriage is loosened from the side rails permitting it to move therealong. This allows the compression spring to provide some compliance to the axial stiffness of the frame, while maintaining the stiffness of the frame in torsion and bending, because load is now transferred from the proximal femoral segment to the half pins of the proximal carriage and then to the compression spring. Depending on the stiffness of the compression spring, the load is then transferred primarily through the proximal bone segment and not through the side rails to any great extent. This applies a compression force at the fracture to promote further healing. In addition, rotation of the rod with the proximal carriage loosened causes at least limited movement of the proximal carriage axially depending on the stiffness of the spring and the direction of rotation of the rod.

The distal carriage is movable with respect to the frame to position the distal bone segment in alignment with the proximal bone segment to reduce the fracture and apply controlled distraction and compression at the fracture site. The distal carriage comprises a pair of spaced, horseshoe shaped plates with opposed, partially spherical shaped sliding surfaces. The sliding surface of the upper horseshoe-shaped plate is concavely arcuate from end-to-end and side-to-side, and the sliding surface of the lower horseshoe-shaped plate is convexly arcuate from end-to-end and side-to-side.

A pin clamping plate or member having at least two and preferably four radially outwardly extending legs is received between the horseshoe shaped plates and slidable between their opposed sliding surfaces. The pin clamping member articulates between the sliding surfaces of the horseshoe plates along a surface defined by a radius of fixed length having its origin at the fracture of the bone. The center of rotation of the pin clamping member is therefore located at the fracture which permits fine or precise adjustment of the position of the distal bone segment since a relatively large motion of the pin clamping member between the horseshoe-shaped plates results in a relatively small movement of the distal bone fragment at the fracture site.

The pin clamping member which supports the distal half pins therefore forms essentially a spherical bearing with the upper and lower horseshoe shaped plates for precise positioning of the distal segment. In addition to such spherical motion, the distal carriage is movable axially along the longitudinally axis of the frame. The lower horseshoe plate is mounted at each side to a pair of clamp arms each having an end adapted to slidably engage one of the side rails of the frame.

The distal and proximal carriages described above are both adapted to clamp half pins which are inserted generally transversely to the longitudinal axes of the distal and proximal bone segments, respectively. In certain situations, physicians prefer that the half pins be inserted at an acute angle relative to one another. In one presently preferred embodiment of this invention, the proximal carriage is modified and comprises two separate pairs of pin clamping sections each movable along the support arms. Each pair of pin clamping sections is formed with a notch for clamping one or more half pins inserted in the proximal segment. The pin clamping sections may be positioned along the support arms by the surgeon to obtain the desired angle of the half pins clamped by each relative to one another.

The external fixation device of this invention may be further modified in another embodiment to accommodate compound or comminuted fractures of the long bones in which one or more central fragments are formed between the distal and proximal bone segments. In these cases, the device of this invention is provided with a fragment support for positioning and immobilizing the central bone fragment between the distal and proximal bone segments.

In one presently preferred embodiment of a fragment support according to this invention, a housing formed with a cavity is mounted to one of the side rails by a flange adapted to slidability engage the side rail. The cavity in the housing pivotally receives a split sphere formed with a central throughbore adapted to receive a half pin inserted within the central fragment. The split sphere is movable within the cavity to position the central fragment as desired, and means are provided to clamp the split sphere in a fixed position within the housing cavity to immobilize the central fragment.

In an alternative embodiment of the fragment support of this invention, upper and lower spaced clamping legs are mounted at one end to one of the side rails of the frame, which receive one split sphere within either an elongated slot formed in each clamping leg, or, in an alternative embodiment, within one of a number of separate seats formed between the clamping legs. A half pin is received within the split sphere to position and immobilize the central bone fragment, and the upper and lower clamping legs are squeezed together at their outer end to secure the split sphere in place therebetween.

In a still further embodiment of the fragment support of this invention, a bracket formed with a seat is slidably mounted to one of the support arms which mounts the proximal carriage. A split sphere identical to those described above is pivotally received within the seat in the bracket to clamp a half pin inserted within the central fragment. Means are provided to clamp the split sphere in a fixed position within the seat to immobilize the central fragment once it has been properly positioned.

In a further aspect of one embodiment of this invention, a drill guide is integrally formed in at least one of the pin clamping sections of the proximal carriage. The drill guide comprises a plurality of spaced bores formed in one of the clamping sections, and each bore is adapted to receive a drill. To use the drill guide, the proximal carriage is moved along its support arms to one side of the frame so as to align the drill guide bores substantially perpendicularly to the longitudinal axis of the proximal bone segment. Drill holes are then made in the proximal segment using the bores as guides, and the proximal carriage is thereafter returned to its original position along the support arms to receive the half pins. In an alternative embodiment, disposable drill guides are provided which are insertable within the notch formed in the proximal and distal carriages to receive and guide the drill.

The drill guide feature of this invention eliminates the need for a reusable drill guide as is often employed in prior art external fixation devices. Because they are separate, such drill guides are often lost.

DESCRIPTION OF THE DRAWINGS

The structure, operation and advantages of a presently preferred embodiment of this invention will become further apparent upon consideration of the following description taken in conjunction with the accompanying drawings, wherein:

FIG. 1 is a plan view in partial cross section of the external fixation device of this invention;

FIG. 2 is a side view in partial cross section taken generally along line 2—2 of FIG. 1;

FIG. 3 is an enlarged side view in partial cross section of the proximal carriage of this invention, taken generally along line 3—3 of FIG. 1;

FIG. 4 is a front view in partial cross section of the distal carriage of this invention, taken generally along line 4—4 of FIG. 2;

DETAILED DESCRIPTION OF THE INVENTION

Figure 5:
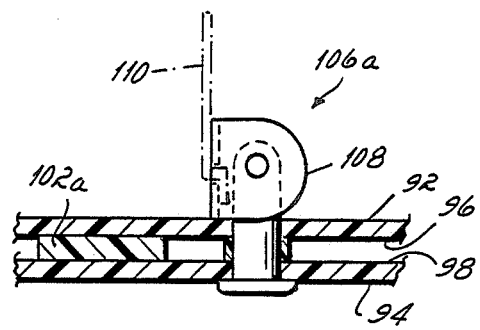
FIG. 5 is a partial cross sectional view of a clamp for the distal carriage of this invention, taken generally along line 5—5 of FIG. 1.

Referring now to FIGS. 1-4, an external fixation device 10 according to this invention is illustrated in a position to align the distal segment 12 and proximal segment 14 at the fracture 16 of a bone 18. The bone 18 is shown schematically, with the fracture 16 in phantom lines, for purposes of illustrating the structure and operation of the fixation device 10 herein. It is contemplated that the device 10 of this invention would be most often utilized to position and immoblize fractures of long bones such as the femur, tibia, humerus, ulna and radius.

The external fixation device 10 includes a frame 20 having opposed side rails 22, 24 connected at each end to a pair of arcuate, end rails 26, 28. As shown in FIG. 3, in one presently preferred embodiment the side rails 22, 24 are generally C-shaped in cross section forming a hollow interior 30. Alternatively, the side rails 22a, 24a are formed with a circular cross section having a solid center. See FIG. 13. Each of the side rails 23, 24, or 22a, 24a, has a foam core 32 preferably made of "Rohacell" polyimide foam. "Rohacell" is a registered trademark of the Cryo Company. In one presently preferred embodiment, the foam core 32 is encased by at least three outer layers 34a-c formed of a fiber material such as glass fiber impregnated with a thermosetting matrix material such as epoxy or a thermoplastic matrix material such as polysulfone. The innermost outer layer 34a is wrapped around the foam core 32 at a 0° angle with respect to its longitudinal axis. The next layer 34b is wrapped at a 45° angle relative to the longitudinal axis of foam core 32 and the outermost layer 34c is wrapped at the same angle as layer 34a. Alternatively, the foam core 32 is encased by one or two layers of a woven or unidirectional fiber reinforced material (not shown) impregnated with a matrix material.

In one embodiment, each of the end rails 26, 28 is generally circular in cross section and is formed with a solid foam core 36 which extends along the length thereof except for the ends. Alternatively, the end rails 26, 28 comprise a hollow or solid flat plate formed of composite material which is arcuate in shape (not shown). The end rails 26, 28 illustrated in the figures are connected to the side rails 22, 24 by L-shaped corner members 38a-d which are preferably formed of "Celcon" plastic. "Celcon" is a registered trademark of Celanese Corporation for an acetal resin. As illustrated in FIG. 1, the corner member 38b, for example, has a generally cylindrical leg 40 which extends into engagement with the foam core 36 of end rail 26. The second leg 42 of the corner member 38b is shaped in the same C-shaped cross section as the side rails 22, 24 and is adapted to fit within the hollow interior 30 of side rail 24. The legs 40, 42 of corner members 36a-d can be either solid or hollow with a tube-shape or other suitable cross section. After insertion of the corner members 38a-d into both the side rails 22, 24 and end rails 26, 28, at least three layers of fibers 39 impregnated with a matrix material are wrapped around the cylindrical leg 40 of the corner members 38a-d, and around the foam core 36 of each end rail 26, 28, to form the completed frame 20. The fibers 39 forming the outer layer of end rails 26, 28 are wrapped at the same angles, and are formed of the same materials, as layers 38a-c described above.

The frame 20 of this invention mounts a proximal carriage 44 at one end and a distal carriage 46 at the other end which are adapted to mount half pins 48 inserted within the proximal segment 14 and distal segment 12, respectively. As shown in FIG. 2, the half pins 48 include a threaded end 50 inserted within the bone 18 and an upper end 52 which extends outwardly from the bone 18 and the soft tissue of the affected limb (not shown).

The proximal carriage 44 is supported on the frame 20 by a pair of support arms 54, 56. Each of the support arms 54, 56 is arcuate in shape from end to end with a middle portion being disposed vertically above the ends which are formed with C-shaped flanges 58, 60. The flanges 58, 60 are adapted to slidably engage the side rails 22, 24, respectively, for movement of the proximal carriage 44 along the longitudinal axis of the frame 20.

Figure 13:
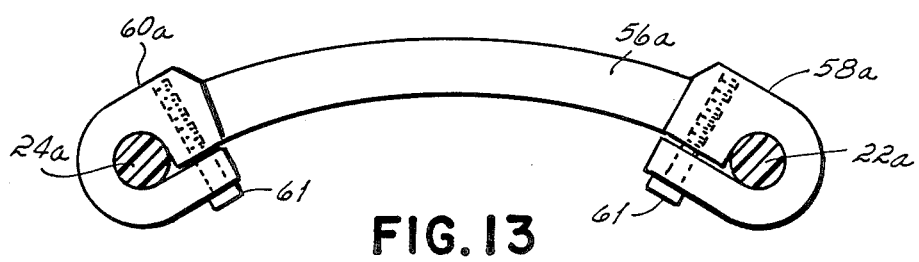
FIG. 13 is a partial cross sectional view of an alternative embodiment of the side rails of the frame herein and the clamp arms of the proximal and distal carriages.

As shown in the embodiment of FIG. 3, the flanges 58, 60 are each secured to the side rails 22, 24 by means of an insert 62 which is formed with the same cross section as the hollow interior 30 of the side rails 22, 24. A threaded sleeve 64 is press fitted into the insert 62, which receives a screw 66 extending through each flange 58, 60 for mounting the support arms 54, 56 to the side rails 22, 24. In the embodiment of FIG. 13, the flanges 58a, 60a of support arms 56a, 58a are C-shaped and extend around the solid core side rails 22a, 24a. The flanges 58a, 60a are clamped in place by screws 61 as shown in FIG. 13.

As best shown in FIGS. 1 and 2, the proximal carriage 44 comprises a pair of pin clamping sections 68, 70 which extend between the support arms 54, 56. Each of the pin clamping sections 68, 70 is formed with a pair of ears 72a, b which are slidably received within elongated notches 74a, b formed in the side walls of the support arms 54, 56, respectively, which face the ears 72a, b. The pin clamping sections 68, 70 have abutting walls 76, 79, respectively, each of which are formed with a cutout so that when the walls 76, 79 contact one another a slot 80 is formed to receive the half pins 48 extending outwardly from the proximal segment 14. As shown in FIG. 1, a pair of elongated screws 82a, b extend between the pin clamping sections 68, 70 to secure them together and to clamp the half pins 48 within the slot 80 formed at their abutting walls 76, 79.

The pin clamping sections 68, 70 are slidable along the support arms 54, 56, transverse to the side rails 22, 24 of frame 20, and are clamped in the desired position therealong by a pair of end caps 84, 86. Each end cap abuts one end of the pin clamping sections 68, 70 and has a downwardly extending leg 87a, b, respectively, which slidably engage the outer wall of the support arms 54, 56. A pair of screws 88a, b extend from end cap 84 to the other end cap 86, through the pin clamping sections 68, 70, for clamping the entire proximal carriage 44 in the desired position along the support arms 54, 56. Screw 88a is disposed within an enlarged bore 89 to permit the pin clamping sections 68, 70 to be spread apart so that the slot 80 formed by their abutting walls 76, 79 can be opened to initially receive the half pins 48 for clamping.

The end cap 84 also preferably includes an extension 180 connected thereto by a pair of screws 182. A plurality of bores 184 are formed at the mating walls of the extension 180 and end cap 84, which extend substantially transverse to the longitudinal axes of side rails 22, 24. Each of the bores 84 is adapted to receive a half pin 48 which is clamped in place by tightening the screws 182. The half pins 48 are clamped between the extension 180 and end cap 84 in patients having a fracture located near the articulating surface of the bone in which cases the proximal segment (not shown) is relatively short in length. To accommodate such cases, the half pins 48 must be inserted across the proximal segment perpendicular to its longitudinal axis rather than along the length of the proximal segment 14 as is done in employing the pin clamping section 68, 70 of the proximal carriage 44. Although shown attached to end cap 84 in FIG. 1, it should be understood that extension 180 could also be attached to end cap 86.

In the embodiment of this invention shown in FIG. 1, the pin clamping section 70 includes a plurality of spaced bores 90 which are formed in a plane generally parallel to the plane of slot 80. The bores 90 form a drill guide 91 to aid in properly locating the half pins 48 along the proximal bone segment 14 so that they can be clamped by the proximal carriage 44. In using the integral drill guide 91 of this invention, the proximal carriage 44 is slid along the support arms 54, 56 toward the upper side rail 22 so that the bores 90 are located approximately where the slot 80 is appears as shown in FIG. 1. A drill (not shown) is then used to form one or more bores in the proximal segment 14, using the bores 90 as a guide, for receiving the half pins 48.

The proximal carriage 44 thus mounts one or more half pins 48 inserted within the proximal segment 14. The proximal carriage 44 is movable with the support arms 54, 56 along the longitudinal axis of the frame 20 so as to adjust the axial position of the proximal segment 14 with respect to the distal segment 12 at the fracture 16. In addition, the proximal carriage 44 is movable along the arcuate support arms 54, 56 in a generally transverse direction relative to the side rails 22, 24. The transverse movement of proximal carriage 44 allows for transverse subluxation of the proximal segment 14 with respect to the longitudinal axis of the distal segment 12. Since the support arms 54, 56 are arcuate, some degree of rotation of the proximal segment 14 is also permitted for further adjustment of its position at the fracture 16.

Referring now to FIGS. 1, 2 and 4, the distal carriage 46 of this invention is illustrated. The distal carriage comprises an upper plate 92 spaced above a lower plate 94, both of which are formed in a generally horseshoe shape. The upper and lower plates 92, 94 are formed in a partial spherical cross section having sliding surfaces 96, 98, respectively, which face one another. The sliding surface 96 of the upper plate 92 is generally concavely arcuate from end-to-end and side-to-side, while the mating sliding surface 98 of the lower plate 94 is generally convexly arcuate from end to end and side to side. A clamping member 100 is sandwiched between the sliding surfaces 96, 98 of the upper and lower plates 92, 94 for pivotal movement therebetween. The clamping member 100 is formed with four radially outwardly extending legs 102a–d, each having the same partial spherical shape as the sliding surfaces 96, 98 to mate therewith.

As best illustrated in FIG. 2, the generally spherical shaped surface of clamping member 100 which contains the legs 102a–d is defined by a radius 104 of fixed length having its origin at the center of the fracture 16 in bone 18. The pivot point of the clamping member 100 for movement between upper and lower plates 92, 94 is therefore at the center of fracture 16, for purposes to become apparent below.

The clamping member 100 is secured between the upper and lower plates 92, 94 by fasteners such as three quick release clamps 106a–c which extend between the upper and lower plates 92, 94. The clamps 106a–c are loosened to permit movement of the clamping 100 therebetween, and are tightened to secure the clamping member 100 in place by the engagement of a cam 108 against the upper plate 92, effected by movement of a lever 110 as illustrated in FIG. 5. Although three clamps 106 are illustrated in the drawings, it is contemplated that the clamp 106c between legs 102c and 102d could be eliminated if desired.

Referring to FIG. 4, the distal carriage 46 is slidably mounted at an acute angle to the side rails 22, 24 of frame 20 by clamp arms 112, 114. Each of the clamp arms 112, 114 includes a bracket 116 connected to the lower plate 94 and an arcuate flange 118 adapted to slidably engage the side rails 22, 24. Inserts 62 identical to those described above are utilized to mount the clamp arms 112, 114 in the desired location along side rails 22, 24, by receiving a screw 115 inserted through the arcuate flanges 118. The same reference numbers are used in FIG. 4 for the identical parts shown in FIG. 3, as discussed in detail above.

The clamping member 100 is formed with a pin clamp 120 for receiving and clamping the half pins 48 inserted within the distal segment 12 of the bone 18. The pin clamp 120 comprises a pair of clamping sections 122, 124 having abutting walls forming a slot 126 therebetween. The half pins 48 are received within the slot 126 and clamped in place by tightening a pair of fasteners such as screws 128a, b which extend between the clamping sections 122, 124. As shown in FIG. 2, the pins 48 are clamped by the pin clamp 120 substantially perpendicularly to the longitudinal axis of bone 18 distally of the fracture 16. The upper and lower plates 92, 94, and clamping member 100, are therefore angled relative to the side rails 22, 24 so that the pivot axis or radius 104 of the clamping member 100 intersects the fracture 16.

Figure 7:
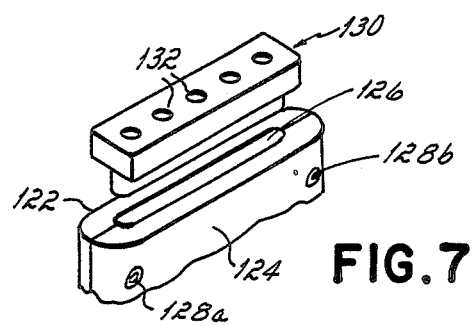
FIG. 7 is a partial isometric view of a disposable drill guide adapted for insertion into the distal or proximal carriage herein.

In a presently preferred embodiment of this invention, the slot 126 of the pin clamp 120 is adapted to receive a disposable drill guide 130 as illustrated in FIG. 7. The drill guide 130 is formed with a plurality of spaced bores 132 which align with the distal segment 12 when the drill guide 130 is inserted into the slot 126. This helps the surgeon properly locate the half pins 48 within the distal segment 12 so that they may be clamped by the distal carriage 46.

An important feature of this invention is the movement of the distal segment 12 provided by the distal carriage 46 herein. Gross or large adjustments in the position of the distal segment 12 are usually made by hand manipulation of the distal portion of the effected limb. For example, in order to provide gross reduction of a fractured tibia the surgeon grasps the ankle and moves the distal segment into general alignment with the proximal segment. The principal function of any external fixation device is to allow the surgeon to make relatively fine or small adjustments in the position of the distal segment after completion of such hand manipulation.

The distal carriage 46 of this invention is specifically designed to permit fine adjustment of the distal bone segment 12 at the site of the fracture 16 for precise alignment with the proximal segment 14. This is achieved by the configuration of the clamping member 100 and sliding surfaces 96, 98 of the upper and lower plates 92, 94, and their angular position with respect to the frame 20. As described above, the clamping member 100 which clamps the half pins 48 inserted within distal segment 12 is pivotal with respect to the sliding surfaces 96, 98 along a surface defined by a radius 104 of fixed length having its origin at the center of fracture 16. In other words, the pivot point of the clamping member 100 is approximately at the center of the fracture 16. Accordingly, the surgeon is permitted to pivot the clamping member 100 substantially while moving the distal segment 12 a comparably small amount at the fracture 16. Unlike prior art fixation devices, in order to obtain small and precise movements of the distal segment 12 at the fracture 16, the surgeon can move the clamping member 100 of the distal carriage 46 herein to a substantial degree which greatly lessens the difficulty of precisely positioning the distal segment 12. In addition, in order to position the clamping member 100 so that its pivot axis or radius 104 intersects the fracture 16, the distal carriage 46 is movable with clamp arms 112, 114 longitudinally along the side rails 22, 24.

Referring now to FIGS. 1, 6 and 8-11, alternative embodiments of a fragment support are illustrated to accommodate compound fractures of a long bone. As is well known, comminuted fractures result in the formation of a separate, central bone fragment (not shown) between the distal and proximal segments 12, 14 which also must be properly positioned and immobilized.

Figure 6:
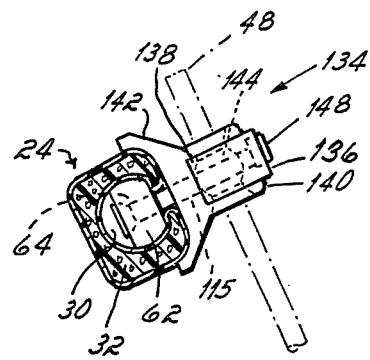
FIG. 6 is a cross sectional view of a medial support in accordance with this invention, taken generally along line 6—6 of FIG. 1.

One embodiment of a fragment support 134 is illustrated in FIGS. 1 and 6. In this embodiment, the fragment support 134 comprises a housing 136 formed with a cavity 138 having a removable end wall 140. The housing 136 is mounted to a flange 142 which is adapted to mount to the side rail 24 between the proximal carriage 44 and distal carriage 46. The flange 142 is slidable along the side rail 24 to position the fragment support 134 longitudinally in the desired location, and then is clamped in place by tightening a screw 115 within an insert 62 disposed in the interior 30 of side rail 24 which is identical to the inserts 62 described in detail above.

The cavity 138 forms a seat which receives a split sphere 144 formed with a central throughbore which is adapted to receive a half pin 48. The split sphere 144 is pivotal within the cavity 138 so as to make fine adjustments in the position of the central fragment relative to the proximal and distal segments 12, 14. Once the central fragment is properly positioned, a screw 148 extending through the cavity end wall 140 and flange 142 into the insert 62 is tightened. The screw 148 urges the end wall 140 against the split sphere 144 to clamp the half pin 48 therewithin, and clamps the flange 142 to the insert 62 for securing the fragment support 134 to the side rail 124.

Figure 8:
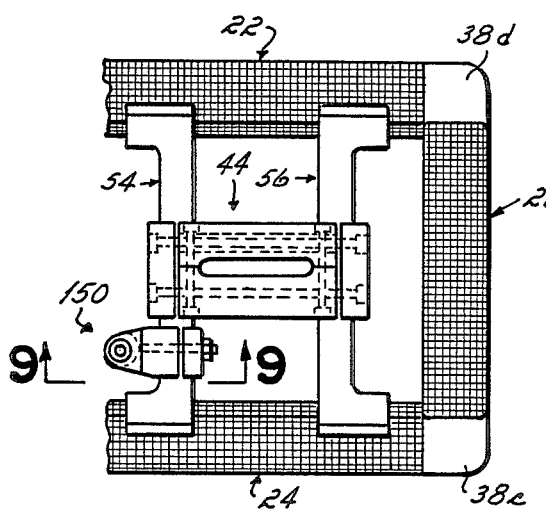
FIG. 8 is a partial plan view of the external fixation device herein having an alternative embodiment of a central fragment support in accordance with this invention.
Figure 9:
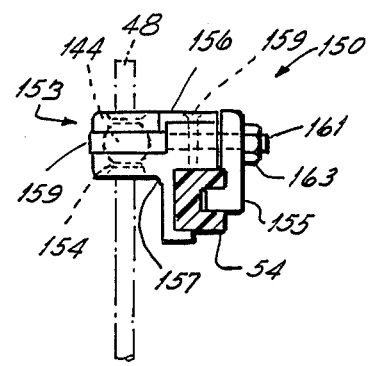
FIG. 9 is an enlarged side view in partial cross section of the central fragment support shown in FIG. 8, taken generally along line 9—9 of FIG. 8.

An alternative embodiment of a fragment support 150 is illustrated in FIGS. 8 and 9. In this embodiment, the fragment support 150 is slidably mounted to the support arm 54 which mounts proximal carriage 44. The fragment support 150 comprises a two-piece bracket including a body portion 153 and end cap 155 which are positioned on opposite sides of the support arm 54. The body portion 153 of the bracket includes a seat 154 formed between a removable top plate 156 and a bottom plate 157 which are connected by a pair of screws 159. The seat 154 pivotally receives a split sphere 144 identical to that described above which mounts a half pin 48 inserted within the central fragment (not shown). An eyelet having a collar 159 and a threaded stem 161 is mounted to the bracket so that its collar 159 extends around the split sphere 144 between the top and bottom plates 156, 157, and its threaded stem 161 extends through the end cap 155. Once the central fragment is properly positioned, a nut 163 is tightened about the threaded stem 161 of the eyelet 158 so as to clamp the split sphere 144 about the half pin 48 and secure the end cap 155 against the support arm 54. This immobilizes the half pin 48 and fixes the fragment support 150 in place along the support arm 54.

Figures 10, 11:
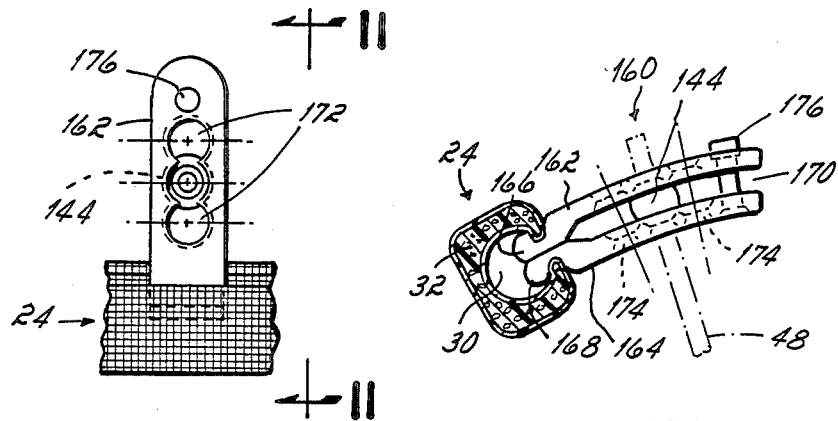
FIG. 10 is a plan view of a still further embodiment of a central fragment support in accordance with this invention.
FIG. 11 is a side view in partial cross section of the central fragment support shown in FIG. 10, taken generally along line 11—11 of FIG. 10.

A still further embodiment of a fragment support 160 is illustrated in FIGS. 10 and 11. Fragment support 160 comprises upper and lower clamping legs 162, 164 which are formed with mating ends 166, 168, respectively, adapted to mount within the interior 30 of a side rail 24. The clamping legs 162, 164 are spaced apart except at their mating ends 166, 168 so as to form a space 170 therebetween. A plurality of bores 172 are formed in the upper clamping leg 162 which align with identical bores 174 formed in the lower clamping leg 164. Each pair of aligning bores 172, 174 form a seat for receiving a split sphere 144, identical to those described above, which is inserted in the space 170 between the clamping legs 162, 164. In an alternative embodiment, the bores 172, 174 are replaced with a continuous, elongated slot (not shown) adapted to receive one or more split spheres 144. A half pin 48 supported by one or more of the split spheres 144 is clamped in place by tightening a screw 176 which extends between the outermost ends of the clamping legs 162, 164. As the screw 176 is tightened, the clamping legs 162, 164 are urged together securing the split sphere 144 in place, and the mating ends 166, 168 tend to be urged apart against the side rail 24 for mounting fragment support 160 securely thereto.

Figure 12:
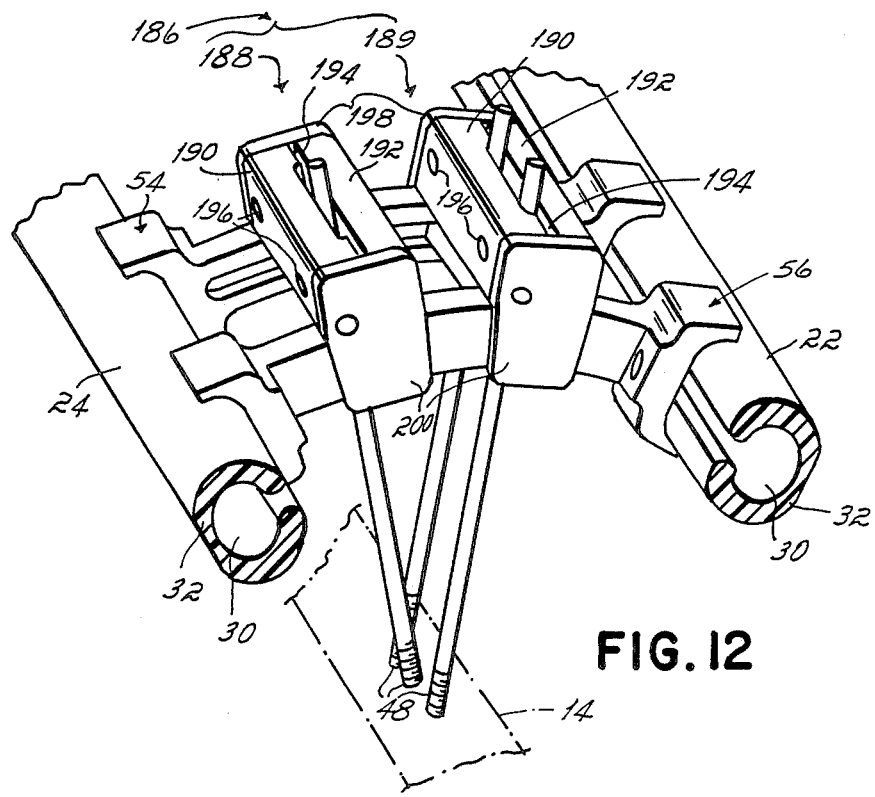
FIG. 12 is a partial perspective view of an alternative embodiment of the proximal carriage of this invention.

Referring now to FIG. 12, an alternative embodiment of a proximal carriage 186 in accordance with this invention is illustrated. In certain applications, it is preferable to insert half pins 48 into the proximal segment 14 at an acute angle with respect to one another. The proximal carriage 186 is a modification of proximal carriage 44 to accomodate such an angled orientation of half pins 48.

The proximal carriage 186 comprises two pin clamping units 188, 189 each including a pair of pin clamping sections 190, 192 which abut one another. The abutting walls of the pin clamping sections 190, 192 of each pin clamping unit 188, 189 form a slot 194 adapted to receive a half pin 48 inserted in the proximal segment 14. Screws 196 extending between the pin clamping sections 190, 192 are tightened to clamp the half pins 48 therebetween. Each of the pin clamping units 188, 189 include end caps 198, 200, which are identical to end cap 86 in FIG. 1, for mounting the pin clamping units 188, 189 to the support arms 54, 56. The pin clamping units 188, 189 are slidable along the support arms 54, 56 to dispose the half pins 48 of each unit 188, 189 at the desired angle relative to one another.

Figure 14:
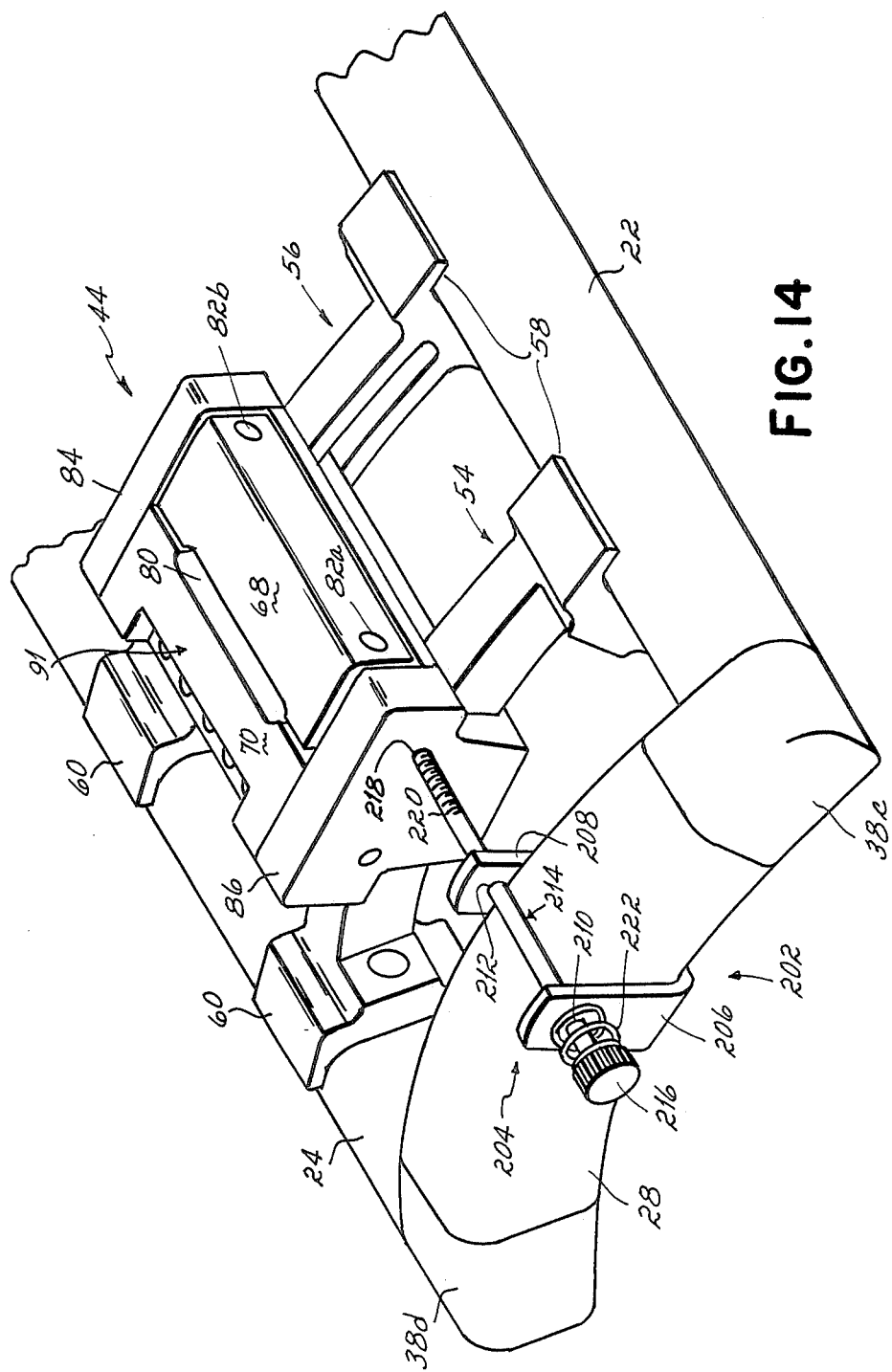
FIG. 14 is a partial perspective view of the proximal carriage of FIG. 1 including a compliance assembly according to this invention.

Referring now to FIG. 14, a still further aspect of this invention is illustrated. The proximal carriage 44, which is identical to that illustrated in FIG. 1 except for the extension 180, is provided with a compliance assembly 202 which functions both to permit relatively small axial adjustments of the proximal carriage 44 along the side rails 22, 24, and also to introduce compliance to the frame 20.

The compliance assembly 202 comprises a U-shaped brace 204 movable along the end rail 28 which includes a pair of upstanding outer and inner legs 206, 208, each formed with a bore 210, 212, respectively. The bores 210, 212 are adapted to receive a rod 214 having a knurled head 216 at one end and a threaded portion 220 extending along the opposite end. The rod 214 is received within the bores 210, 212 of brace 204 so that the threaded portion 220 threadedly engages an internally threaded bore 218 formed in the end cap 86 of the proximal carriage 44. A compression spring 222 is positioned between the head 216 of rod 214 and the outer leg 206 of brace 204.

Axial adjustment of the proximal carriage 44 along the side rails 22, 24 is accomplished by first loosening the engagement of the proximal carriage 44 to the side rails 20, 22 and then rotating the rod 214 so that its threaded portion 220 rotates within the threaded bore 218 in the end cap 86. The proximal carriage 44, in turn, is thus moved axially with respect to the longitudinal axis of the frame 20, with the direction of axial movement depending upon the direction of rotation of the rod 214 and the extent of axial movement depending upon the stiffness of compression spring 222.

Another purpose of the compression spring 222 in the compliance assembly 202 of this invention is to introduce compliance to the frame 20 at desired stages of the healing process of the fracture 16. During the initial stages of treatment of a fractured bone, when the proximal and distal fragments have not yet begun to fuse together, the proximal carriage 44 is clamped in a fixed position to the side rails 22, 24 as described in detail above. Forces applied by the patient's weight in moving about are therefore transferred from the proximal segment 14, to the proximal carriage 44 through the half pins 48, along the side rails 22, 24 of the frame 20 and then through the distal carriage 46 to the distal segment 12. With the proximal carriage 44 secured to the side rails 22, 24, the frame 20 functions as a bridge over the fracture 16 between the proximal and distal segments 14, 12. Little or no load is applied to the fracture itself because the forces are transferred directly from the proximal segment 14 to the distal segment 12 through the frame 20.

As is well known, the addition of load to a bone fracture urging the proximal and distal segments together aids the healing process. The function of compression spring 222 in this aspect of the invention is to provide for loading at the fracture 16 by reducing the axial stiffness of the frame, while maintaining the stiffness of the frame 20 in both torsion and bending. This is accomplished by loosening the connections of the support arms 54, 56 to the side rails 22, 24 so that the proximal carriage 44 is slidable therealong. Once the proximal carriage 44 is loosened, the load path from the proximal segment 14 to the distal segment 12 no longer follows the side rails 22, 24 of the frame but is applied across the fracture 16. Upon placing weight on the proximal bone segment 14, load is transferred through the half pins 48 in the proximal segment 14 to the proximal carriage 44. Since the proximal carriage 44 is loosened along the side rails 22, 24, the load is then transferred from the proximal carriage 44 to the compression spring 222. Depending on the stiffness of the compression spring 222, the load is then transferred primarily back through the proximal carriage 44 and half pins 48 to the proximal bone segment 14 rather than along the side rails 22, 24. This results in the application of a compression force at the fracture 16 to promote further healing. The amount of load applied at the fracture 16 is controlled by varying the stiffness of the compression spring 222, or the compliance of the frame 20, so that a varying amount of load may be applied to the fracture 16 instead of the side rails 22, 24.

While the invention has been described with reference to a preferred embodiment, it will be understood by those skilled in the art that various changes may be made and equivalents may be substituted for elements thereof without departing from the scope of the invention. In addition, many modifications could be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:
1. An external fixation device for positioning and immobilizing the distal segment and proximal segment of a fractured bone to reduce the fracture comprising:
    a frame having a proximal carriage mounted at one end and a distal carriage mounted at the other end;

said proximal carriage being adapted to clamp half pins inserted in the proximal segment of the fractured bone, said proximal carriage being movable with respect to said frame to adjust the position of the proximal segment;

said distal carriage including a clamping element adapted to clamp half pins inserted in the distal segment of the fractured bone, said clamping element being movable with respect to said distal carriage along a partially spherical-shaped surface defined by a radius of fixed length having an origin at the approximate center of the fracture so as to permit precise adjustment of the position of the distal segment at the fracture for alignment with the proximal segment.

2. An external fixation device for positioning and immobilizing the distal segment and proximal segment of a fractured bone to reduce the fracture, comprising:

a frame having opposed side rails connected at each end to an end rail;

a proximal carriage adapted to clamp half pins inserted in the proximal segment of the fractured bone;

first mounting means for mounting said proximal carriage to said side rails, said proximal carriage being movable relative to said first mounting means and relative to said frame to adjust the position of the proximal segment;

a distal carriage including a support for mounting a clamping element, said clamping element being adapted to clamp half pins inserted in the distal segment of the fractured bone, said clamping element being movable with respect to said distal carriage along a partially spherical-shaped surface defined by a radius of fixed length having an origin at the approximate center of the fracture to adjust the position of the distal segment at the fracture;

second mounting means for mounting said distal carriage to said side rails, said distal carriage being movable with said second mounting means relative to said frame to adjust the position of the distal segment at the fracture.

3. The device of claim 2 in which each of said side rails is formed with a core of foam material and at least one outer layer of composite material wrapped about said core of foam material.

4. The device of claim 3 in which said core of foam material is formed of polyimide foam.

5. The device of claim 3 in which said at least one outer layers of composite material comprises a first layer wrapped over said core of foam material at an angle of 0° relative to the longitudinal axis thereof, a second layer wrapped over said first layer at an angle of plus or minus 45°, and a third layer wrapped over said second layer at an angle of 0°.

6. The device of claim 3 in which each of said outer layers are formed of graphite or glass fibers, said fibers being impregnated with a matrix material chosen from the group consisting of thermosetting and thermoplastic resins.

7. The device of claim 2 further including a pair of spaced support arms mounted between said side rails, said proximal carriage comprising:

a pair of pin clamping sections extending between said support arms, said pin clamping sections having abutting walls forming a slot therebetween to receive half pins;

first means for clamping said pin clamping sections together to secure the half pins within said slot;

a pair of end caps disposed at opposite ends of said pin clamping sections, each of said end caps engaging one of said support arms;

second means for releasably clamping said end caps to said pin clamping sections and to said support arms for securing said pin clamping sections in a fixed position along said support arms.

8. The device of claim 7 in which said first means comprises at least two elongated screws extending between said pin clamping sections transverse to said slot, said screws being tightened to clamp said pin clamping sections together.

9. The device of claim 7 in which said second means comprises at least two elongated screws extending from one end cap to the other end cap through said pin clamping sections disposed therebetween, said screws being tightened to clamp said end caps against said pin clamping sections and against said arm supports.

10. The device of claim 7 in which each said end caps is formed with an outer wall, said device further including an extension having a wall abutting said outer wall of one of said end caps, a plurality of bores being formed between said abutting walls of said extension and said end cap substantially transverse to the longitudinal axis of the fractured bone, and a pair of screws extending between said extension and said end cap, each of said bores being adapted to receive a half pin, the half pins being clamped within said bores upon tightening said screws.

11. An external fixation device for positioning and immobilizing the distal segment and proximal segment of a fractured bone to reduce the fracture, comprising:

a frame having opposed side rails connected at each end to an end rail;

a proximal carriage adapted to clamp half pins inserted in the proximal segment of the fractured bone;

first mounting means for mounting said proximal carriage to said side rails, said proximate carriage being movable relative to said first mounting means and relative to said frame to adjust the position of the proximal segment;

a distal carriage comprising:
(i) a support including spaced upper and lower plates;
(ii) a clamping element movable between said upper and lower plates along a partially spherical-shaped surface defined by a radius of fixed length having an origin at the approximate center of the fracture;
(iii) means for releasably connecting said upper and lower plates to permit sliding motion of said clamping element therebetween; and
(iv) means for mounting said lower plate to each of said side rails.

12. The device of claim 11 in which said clamping element comprises a center section having an elongated slot adapted to mount a pin clamping block, and at least two legs extending radially outwardly from said center section between said spaced upper and lower plates.

13. The device of claim 12 in which said center section and said legs of said clamping element form a sliding surface defined by a radius of fixed length having its origin at the fracture.

14. The device of claim 13 in which said upper and lower plates are formed in a horseshoe shape with opposed sliding surfaces which are partially spherical in shape, said sliding surfaces receiving said clamping element therebetween, said clamping element being movable with respect to said sliding surfaces to align the distal segment with the proximal segment.

15. The device of claim 11 in which said means for mounting said lower plate to each of said side rails comprises a clamp arm having a bracket connected to said lower plate and an arcuate flange adapted to slidably engage said side rail.

16. The device of claim 15 in which said side rails are formed with a C-shaped cross section having a hollow center, said means for mounting said lower plate to said side rails further comprising an insert having substantially the same cross section as said hollow center of said side rails, one of said inserts being insertable within said hollow center of each of said side rails and into alignment with one of said arcuate flanges, each of said inserts being formed with a threaded sleeve adapted to receive a screw extending through said arcuate flange for mounting said clamp arm and said lower plate to said side rails.

17. An external fixation device for positioning and immobilizing the distal segment and proximal segment of a fractured bone to reduce the fracture, comprising:
a frame having a proximal carriage mounted at one end and a distal carriage mounted at the other end;
said proximal carriage being formed with drill guide means for aligning a drill with respect to the proximal segment of the fractured bone to permit the insertion of half pins within the proximal segment;
said proximal carriage having means for clamping half pins inserted in the proximal segment, said proximal carriage being movable with respect to said frame to adjust the position of the proximal segment at the fracture;
said distal carriage including a clamping element adapted to clamp half pins inserted in the distal segment of the fractured bone, said clamping element being movable with respect to said distal carriage along a partially spherical-shaped surface defined by a radius of fixed length having an origin at the approximate center of the fracture so as to permit precise adjustment of the position of the distal segment at the fracture for alignment with the proximal segment.

18. The device of claim 17 in which said frame includes a pair of opposed side rails, and said proximal carriage is movable relative to said side rails along a pair of support arms slidably mounted to said side rails, said drill guide means comprising a plurality of spaced bores formed in said proximal carriage between said support arms, said proximal carriage being movable along said support arms to align said spaced bores of said drill guide means with the proximal segment.

19. The device of claim 17 in which said proximal carriage and said distal carriage are each formed with an elongated slot adapted to receive a drill guide, said drill guide being formed with a plurality of holes for alignment with the distal and proximal segments.

20. An external fixation device for positioning and immobilizing the distal segment, proximal segment and at least one central fragment therebetween of a bone having a comminuted fracture to reduce the fracture, comprising:
a frame having opposed side rails connected to each end to a pair of opposed end rails;
a carriage support mounted to said side rails and slidable axially therealong;
a proximal carriage adapted to clamp half pins inserted in the proximal segment of the fractured bone, said proximal carriage being mounted upon said carriage support and movable therewith relative to said side rails to adjust the position of the proximal segment with respect to said central fragment;
a fragment support adapted to clamp at least one half pin inserted in the central fragment of the fractured bone, said fragment support being mounted to one of said carriage support and said side rails;
a distal carriage including a clamping element adapted to clamp half pins inserted in the distal segment of the fractured bone, said clamping element being movable with respect to said distal carriage along a partially spherical-shaped surface defined by a radius of fixed length having an origin at the approximate center of the fracture so as to permit precise adjustment of the position of the distal segment at the fracture for alignment with the central fragment.

21. The device of claim 20 in which said fragment support comprises:
a flange adapted to slidably mount to one of said side rails;
a housing formed with a cavity having one removable end wall, said housing being connected to said flange;
a split sphere formed with a central throughbore adapted to receive a half pin, said split sphere being pivotally received within said cavity;
means for urging said removable end wall against said split sphere to clamp the half pin therewithin.

22. The device of claim 20 in which said fragment support comprises:
a split sphere formed with a throughbore adapted to receive a half pin;
upper and lower spaced clamping legs mounted at one end to one of said side rails, said upper and lower clamping legs being formed with means for receiving said split sphere therebetween;
means for clamping said upper and lower clamping legs together to secure said split spheres therebetween and to clamp the half pins within said split sphere.

23. The device of claim 20 in which said fragment support comprises:
a bracket slidably mounted to said carriage support, said bracket being formed with a seat having a removable wall;
a split sphere formed with a throughbore adapted to receive a half pin, said split sphere being pivotally received within said seat; and
means for clamping said split sphere within said seat for securing a half pin within said split sphere.

24. An external fixation device for positioning and immobilizing the distal segment and proximal segment of a fractured bone to reduce the fracture, comprising:
a frame having a proximal carriage mounted at one end and a distal carriage mounted at the other end;
said proximal carriage being formed with two pin clamping units, each of said pin clamping units being adapted to clamp half pins inserted within the proximal segment, said pin clamping units being movable with respect to said frame independently of one another to dispose the half pins at an acute angle relative to one another;

said distal carriage including a clamping element adapted to clamp half pins inserted in the distal segment of the fractured bone, said clamping element being movable with respect to said distal carriage along a partially spherical-shaped surface defined by a radius of fixed length having an origin at the approximate center of the fracture so as to permit precise adjustment of the position of the distal segment at the fracture for alignment with the proximal segment.

25. The device of claim 24 in which each of said pin clamping units includes a pair of pin clamping sections joined together at abutting walls and forming a slot thereat, said slot of each said pin clamping units being adapted to receive at least one half pin.

26. An external fixation device for positioning the distal segment and proximal segment of a fractured bone to reduce the fracture comprising:

a frame having a pair of spaced side rails connected to a pair of end rails;

a proximal carriage mounted to said side rails of said frame, said proximal carriage being adapted to clamp half pins inserted in the proximal segment of the fractured bone;

compliance means connected to said proximal carriage for transferring load applied to the fractured bone from the proximal segment across the fracture to the distal segment;

a distal carriage mounted to said side rails of said frame, said distal carriage including a clamping element adapted to clamp half pins inserted in the distal segment of the fractured bone, said clamping element being pivotal about the fracture so as to permit precise adjustment of the position of the distal segment for alignment with the proximal segments.

27. The device of claim 26 in which said proximal carriage is formed with an end cap having a threaded bore, said compliance means comprising:

a bracket movable along one of said end rails, said bracket having inner and outer upstanding legs straddling said end rail, each of said legs being formed with a bore;

a rod having a head at one end and a threaded portion at the other end;

said rod being received within said bores of said inner and outer legs so that said threaded portion is received within said threaded bore in said end cap of said proximal carriage and said head is spaced from said outer leg of said bracket; and a compression spring disposed between said head of said rod and said outer leg of said bracket.

* * * * *